(12) United States Patent
Bjorn et al.

(10) Patent No.: US 11,166,752 B2
(45) Date of Patent: *Nov. 9, 2021

(54) MEDICAL IMPLANT SYSTEM

(71) Applicant: Cochlear Limited, Macquarie University (AU)

(72) Inventors: Goran Bjorn, Onsala (SE); Marcus Andersson, Gothenburg (SE)

(73) Assignee: Cochlear Limited, Macquarie University (AU)

( * ) Notice: Subject to any disclaimer, the term of this patent is extended or adjusted under 35 U.S.C. 154(b) by 1467 days.

This patent is subject to a terminal disclaimer.

(21) Appl. No.: 15/049,895

(22) Filed: Feb. 22, 2016

(65) Prior Publication Data

US 2016/0242814 A1     Aug. 25, 2016

Related U.S. Application Data

(60) Division of application No. 13/371,763, filed on Feb. 13, 2012, now Pat. No. 9,271,092, which is a continuation of application No. PCT/US2010/000401, filed on Apr. 9, 2010.

(30) Foreign Application Priority Data

Aug. 13, 2009   (AU) ................................ 2009903789
Oct. 14, 2009   (AU) ................................ 2009905020

(51) Int. Cl.
  *H04R 25/00*    (2006.01)
  *A61B 17/68*    (2006.01)

(52) U.S. Cl.
  CPC ......... *A61B 17/686* (2013.01); *H04R 25/606* (2013.01)

(58) Field of Classification Search
  CPC ..................... H04R 25/606; Y10T 403/4991
  See application file for complete search history.

(56) References Cited

U.S. PATENT DOCUMENTS

| 4,498,461 A | 2/1985 | Hakansson |
| 5,447,434 A * | 9/1995 | Shaw ................. A61C 8/005 403/285 |
| 5,702,342 A | 12/1997 | Metzler et al. |
| 5,735,790 A | 4/1998 | Hakansson et al. |

(Continued)

FOREIGN PATENT DOCUMENTS

WO       9855049 A1    12/1998

OTHER PUBLICATIONS

International Search Report and Written Opinion for PCT/AU2010/000401, dated Jun. 3, 2010.

(Continued)

*Primary Examiner* — Samuel S Hanna
(74) *Attorney, Agent, or Firm* — Piloff Passino & Cosenza LLP; Martin J. Cosenza

(57) ABSTRACT

An implant including a bone fixture configured to anchor to bone of a recipient, and a structural component configured to be connected to the bone fixture and connect a functional component of the implant to the bone fixture, wherein at least one of the bone fixture or the structural component includes a deformable element configured to deform to form an anti-microbial seal between the bone fixture and the structural component, and the at least one deformable element and the respective at least one bone fixture or structural component form a monolithic structure.

23 Claims, 21 Drawing Sheets

(56) References Cited

U.S. PATENT DOCUMENTS

| | | | |
|---|---|---|---|
| 6,447,295 B1 | 9/2002 | Kumar et al. | |
| 7,065,223 B2* | 6/2006 | Westerkull | H04R 25/606 |
| | | | 381/151 |
| 2003/0124491 A1* | 7/2003 | Honkura | A61C 8/005 |
| | | | 433/189 |
| 2005/0014108 A1* | 1/2005 | Wohrle | A61C 8/0066 |
| | | | 433/173 |
| 2006/0050913 A1 | 3/2006 | Westerkull | |
| 2009/0075236 A1* | 3/2009 | Towse | A61C 8/0012 |
| | | | 433/174 |
| 2009/0082817 A1* | 3/2009 | Jinton | H04R 25/606 |
| | | | 606/301 |
| 2012/0172658 A1 | 7/2012 | Bjorn et al. | |

OTHER PUBLICATIONS

European Search Report and Search Opinion for European Application No. 10807771.0 dated Feb. 25, 2013.
European Search Report and Search Opinion for European Application No. 15191774.7 dated Feb. 1, 2016.
European Examination Report for European Application No. 15191774.7 dated Aug. 3, 2017.
Office Action in EP Application No. 15 191 774.7, dated Jul. 4, 2018.

* cited by examiner

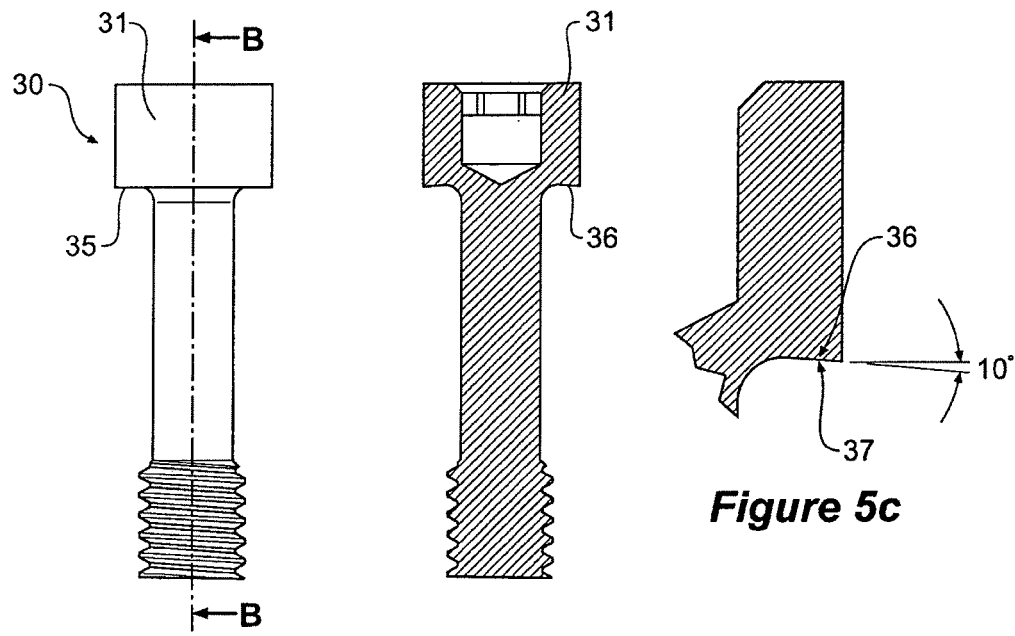
*Figure 5a*   *Figure 5b*   *Figure 5c*
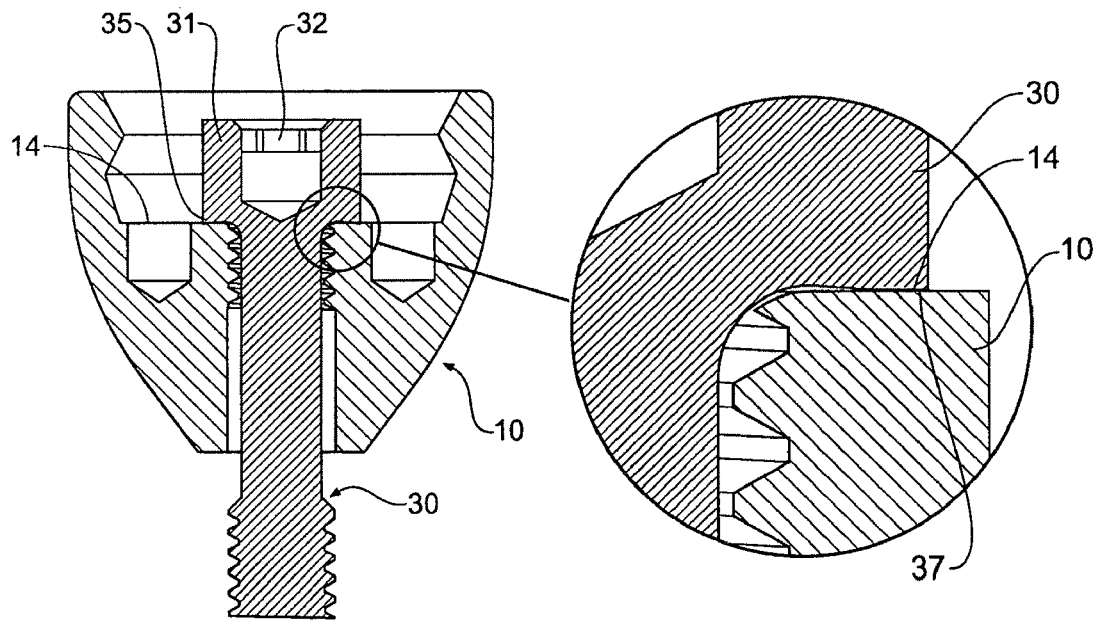
*Figure 6*   *Figure 7*

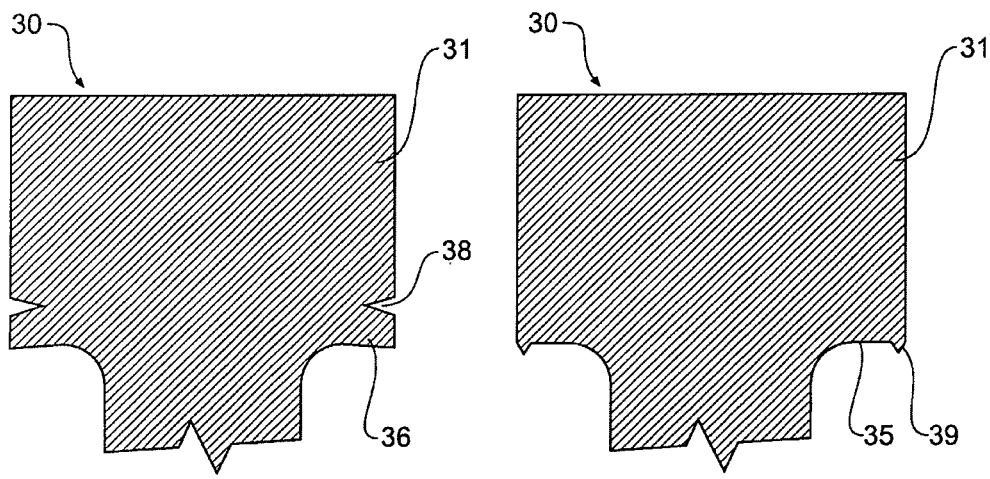
*Figure 8*      *Figure 9a*
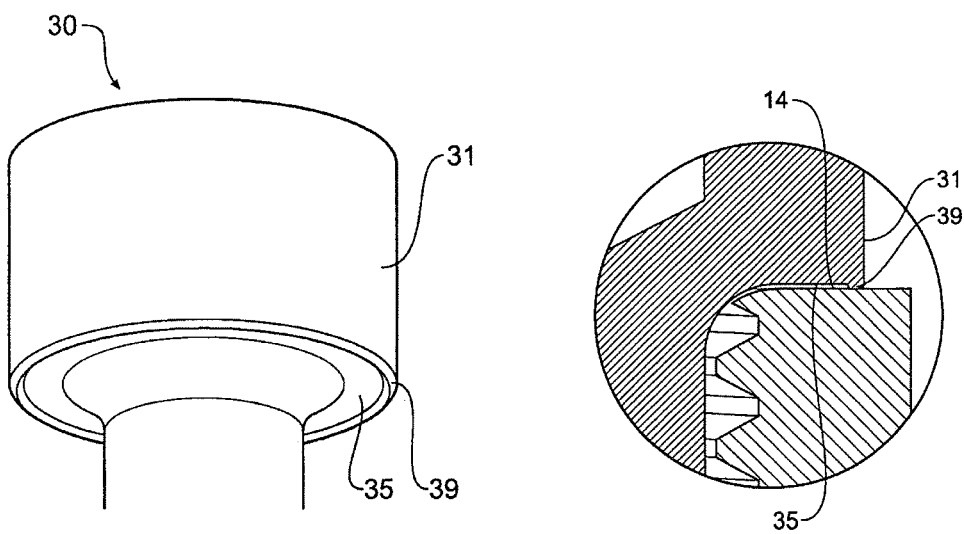
*Figure 9b*      *Figure 10*

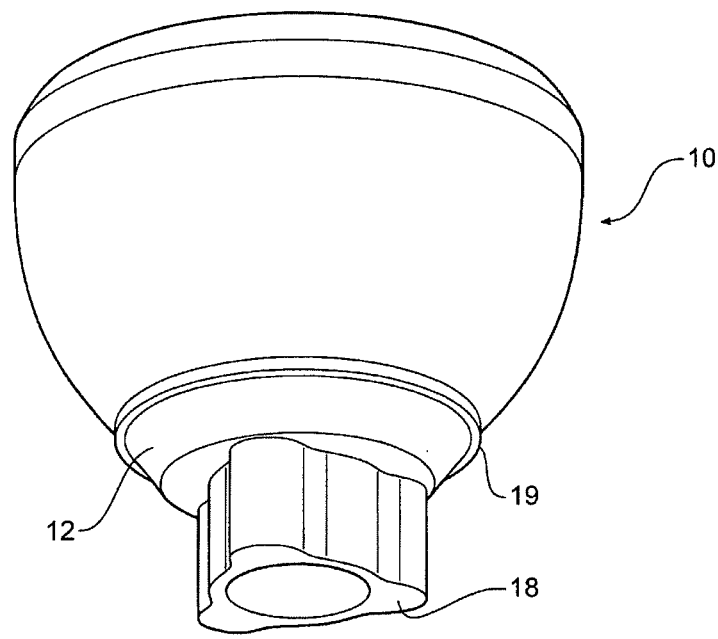
Figure 20
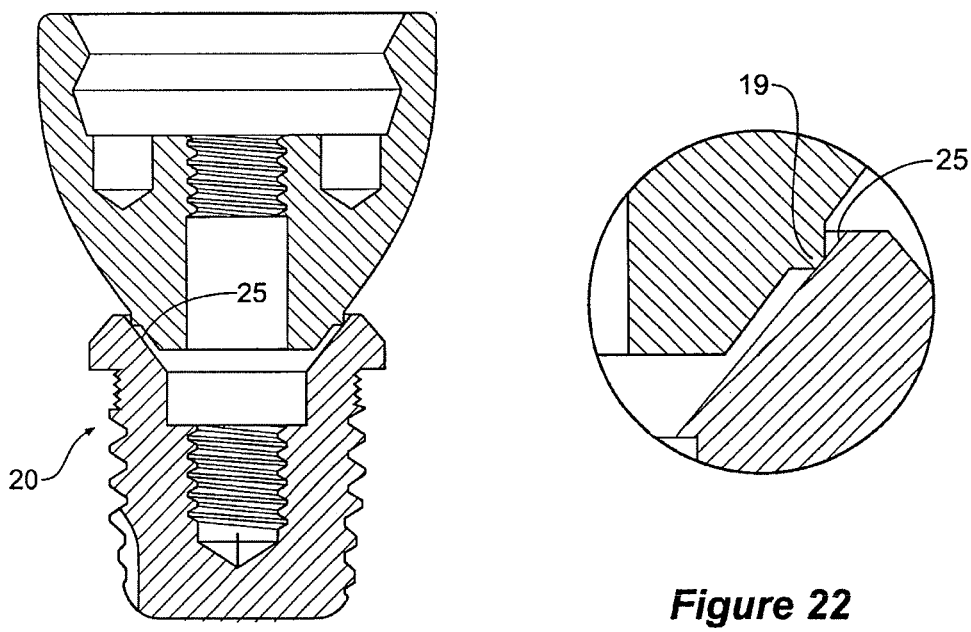
Figure 21
Figure 22

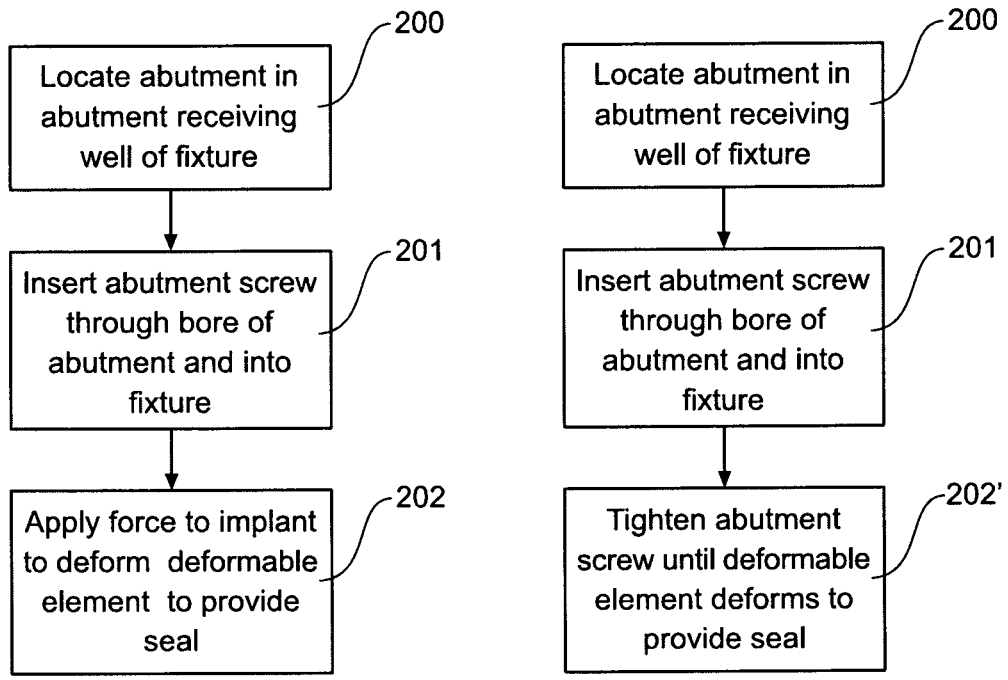
*Figure 26a*
*Figure 26b*
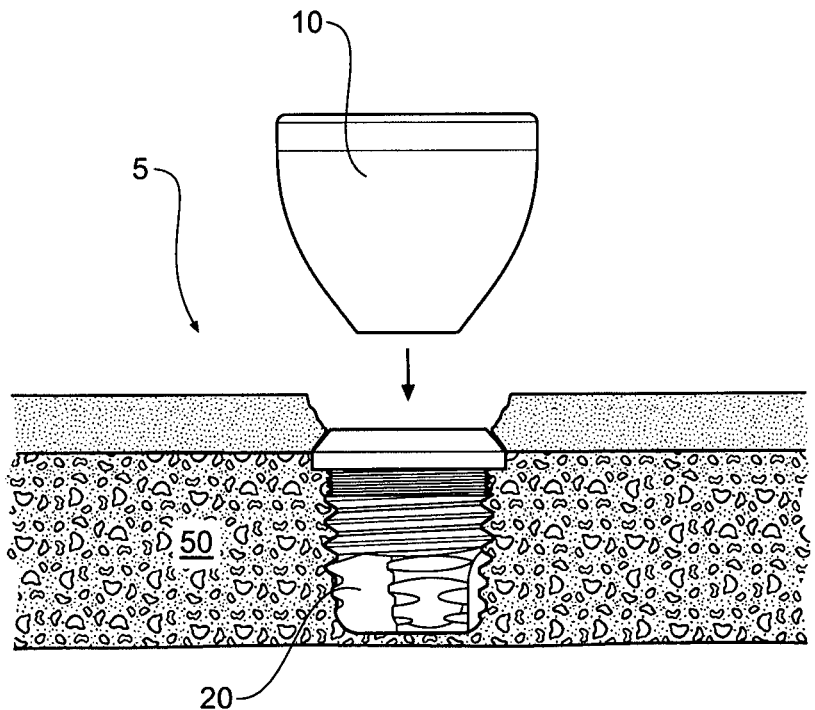
*Figure 27a*

MEDICAL IMPLANT SYSTEM

CROSS-REFERENCE TO RELATED APPLICATIONS

The present application is a divisional application of U.S. patent application Ser. No. 13/371,763, filed Feb. 13, 2012, which is a continuation application of International Patent Application No. PCT/AU2010/000401, filed on Apr. 9, 2010, designating Goran Bjorn of Sweden and Dr. Marcus Andersson, also of Sweden, as inventors, which claims priority to Australian Provisional Patent Application No. 2009903789 entitled "Implant Device" filed on 13 Aug. 2009, and Australian Provisional Patent Application No. 2009905020 entitled "Implant Device" filed on 14 Oct. 2009, the entire content of each of these applications being hereby incorporated by reference herein in their entirety.

BACKGROUND

Field of the Invention

The present invention relates generally to bone conduction devices, and more particularly, to infection prevention measures associated with percutaneous bone conduction devices.

Related Art

Bone-anchored medical implant systems are used to connect or fixate hearing devices to a recipient, directly to the bone or skull of the recipient. Some applications include hearing implants such as bone conduction devices marketed by Cochlear Bone Anchored Solutions AB in Sweden. Such bone conduction devices sometimes comprise, in the case of percutaneous bone conductions devices as is shown by way of example in FIG. 27d in black-box format, an external, removable unit 2759 including a vibrator 2761 which transforms sound into mechanical vibrations. Percutaneous bone conductions devices conduct those mechanical vibrations via an abutment 2763 and a bone fixture 2765 of the implant, into the bone of the skull. Passive transcutaneous bone conduction devices conduct those mechanical vibrations through skin of the recipient to an implantable component which includes a bone fixture. The vibrations are transmitted mechanically via the skull bone and thereafter to the inner ear of a person with impaired hearing and allows for the hearing organ to register the sound. A hearing device of the bone conduction device type typically includes an anchoring element or fixture, in the form of, for example, an implanted titanium screw, corresponding to the bone fixture, installed in the bone behind the external ear and the sound is transmitted via the skull bone to the cochlea (inner ear), irrespective of any disease, injury or other dysfunction of the middle ear. In percutaneous bone conduction or anchoring arrangements, the skin is penetrated, which makes the vibratory transmission very efficient. This arrangement can also be used in connection with facial prostheses, such as, for example, some of those marketed by Cochlear Limited, Australia.

The implants which are used with percutaneous bone conduction devices are sometimes provided in two pieces. One piece comprises the screw-shaped anchoring element (fixture or anchor) and the other piece comprises the abutment, which penetrates the skin. This two-piece design, in many exemplary embodiments, allows the surgical implantation to be carried out as a two-step procedure. In the first step of implanting such a two-pieced design, the fixture is inserted and maintained unloaded during a healing period of some months or so. After this healing period the second step of the surgical procedure, i.e. the connection of the abutment by means of an abutment screw, is executed. The two-part design may allow for the implants to be up-graded, if desirable, without removing the fixture or anchor. Furthermore, if the abutment is damaged, it can then be replaced without need of removal of the bone anchored screw or fixture.

A situation sometimes experienced with bone conduction devices in general, and percutaneous implant devices in particular, is the risk of infections and inflammation. This exists sometimes at the tissue-implant interface. The infections are a result of bacterial colonization at the area around the interface between the bone fixture and the abutment. This problem can be persistent and cause infections. Cleaning of the interface has utility, but even regular cleaning and disinfection is not always entirely successful. The risk of infections may also exist at the interface between separate components of totally implantable prostheses.

With respect to a percutaneous bone conduction device, the bacteria may enter the implant tissue interface by two different routes—an external route on the external surface of the abutment, and an internal route which starts at the top of the abutment and travels via internal parts (screw connection) of the implant system and may exit at the abutment-fixture-soft tissue junction or interface. The external route is the most open route, but the bacteria may also reach the implant-tissue interface from the internal route, known as the internal micro-leakage pathway.

SUMMARY

Some aspects of the present invention are generally directed to an implant including a bone fixture configured to anchor to bone of a recipient, and a structural component configured to be connected to the bone fixture and connect a functional component of the implant to the bone fixture, wherein at least one of the bone fixture or the structural component includes a deformable element configured to deform to form an anti-microbial seal between the bone fixture and the structural component, and the at least one deformable element and the respective at least one bone fixture or structural component form a monolithic structure.

Some other aspects of the present invention are generally directed to an implant, comprising a bone fixture configured to anchor to bone of a recipient, a structural component configured to be connected to the bone fixture and connect a functional component of the implant to the bone fixture, and a screw configured to bolt the structural component to the bone fixture, wherein the implant includes an anti-microbial seal between the structural component and the screw.

Some other aspects of the present invention are generally directed to an implant, comprising, a bone fixture configured to anchor to bone of a recipient, and a structural component configured to be connected to the bone fixture and connect a functional component of the implant to the bone fixture, wherein at least one of the bone fixture or the structural component includes a deformable element configured to plastically deform to form an anti-microbial seal between the bone fixture and the structural component.

Some other aspects of the present invention are generally directed to a method of attaching an abutment to an implanted bone fixture to form a percutaneous implant, comprising positioning the abutment in contact with the implanted bone fixture, and applying a torque of about 15 Ncm or more to a component of the percutaneous implant threadably engaged with the implanted bone fixture, thereby driving the abutment towards the bone fixture via reaction against the implanted bone fixture, wherein the applied torque is sufficient to at least one of deform material of at least one of the bone fixture and the abutment to form an anti-microbial seal between the hone fixture and the abutment, or deform material of at least one of an abutment screw and the abutment to form an anti-microbial seal between the abutment screw and the abutment.

BRIEF DESCRIPTION OF THE DRAWINGS

Embodiments of the present invention are described below with reference to the attached drawings, in which:

FIG. 5*a*—shows one embodiment of an abutment screw of one aspect of the disclosure;

FIG. 5*b*—shows a cross section of the abutment screw of FIG. 5A;

FIG. 5*c*—shows a close up view of the deformable element of FIG. 5B;

FIG. 6—shows a cross section of the abutment screw of FIG. 5A in an abutment;

FIG. 7—shows a close-up cross section view of a seal provided between the abutment screw of FIG. 5A and the abutment;

FIG. 8—shows a cross section of an alternative embodiment of the abutment screw of FIG. 5A;

FIG. 9*a*—shows a cross section of yet a further alternative of the abutment screw of FIG. 5A;

FIG. 9*b*—shows a perspective view of the abutment screw of FIG. 9A;

FIG. 10—shows a close-up cross section view of a seal provided between the abutment screw of FIG. 9*a* and the abutment;

FIG. 20—shows a different embodiment of an abutment;

FIG. 21—shows the abutment of FIG. 20 engaging with a fixture;

FIG. 22—shows a close-up of a seal provided by the arrangement of FIG. 21;

FIG. 26*a*—shows a flow chart of a method of implanting a medical implant system;

FIG. 26*b*—shows a specific example of the method of FIG. 26*a*;

FIG. 27*a*—shows a cross section of the arrangement of the first step of the method of FIG. 26*b*;

DETAILED DESCRIPTION

Figure 1:
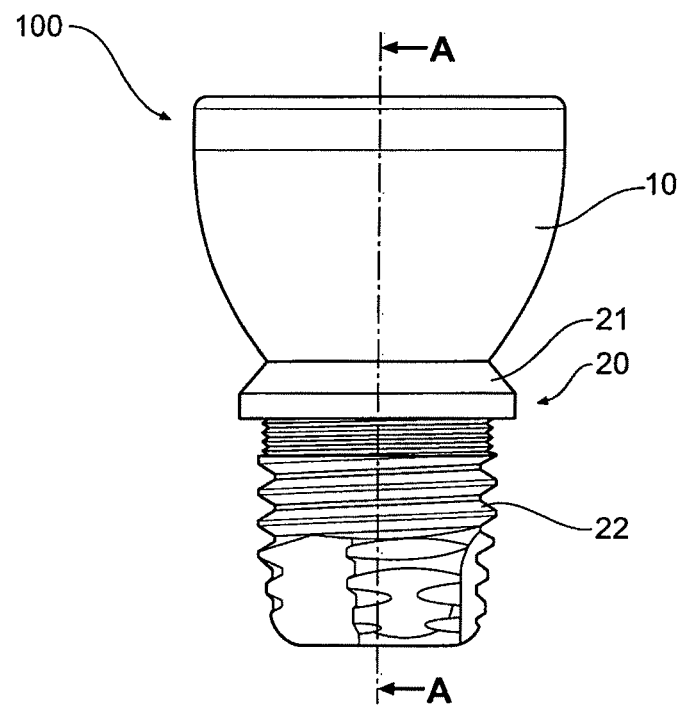
FIG. 1—shows an example of a medical implant system to which various aspects of the present disclosure may be applied.

FIG. 1 shows a side view of a medical implant system 100. The implant system has an abutment 10 that enables a hearing device to be coupled through a percutaneous connection to a bone anchoring device in the form of fixture 20. Abutment 10 is connected to fixture 20. Fixture 20 has a base collar 21 and screw threads 22. In use, screw threads 22 is screwed into bone of the recipient (sometimes herein also referred to as the user) to fixate and retain fixture 20 to the user's skull.

Figure 2:
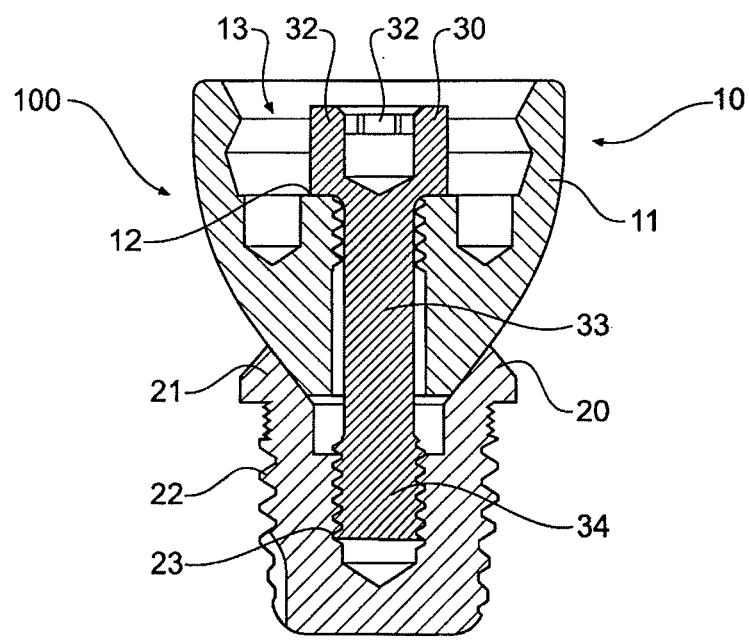
FIG. 2—shows a cross section of the medical implant system of FIG. 1.

As can be seen in FIG. 2, which shows a cross section view along the line A-A' of FIG. 1, abutment 10 is connected to and retained to fixture 20 by abutment screw 30. Abutment screw 30 has head 31, a well 32 within the head 31 to receive an insertion tool or the like, and an apical outer screw threaded section 34 on an elongate main body 33. In some examples, abutment screw 30 may be an M 1.8 titanium screw and the well 32 in head 31 may be a tubular hex configuration for receiving and cooperating with the insertion tool (not shown). The apical outer screw threaded section 34 engages with inner screw thread 23 of the fixture 20 upon turning of the insertion tool.

Figure 3:
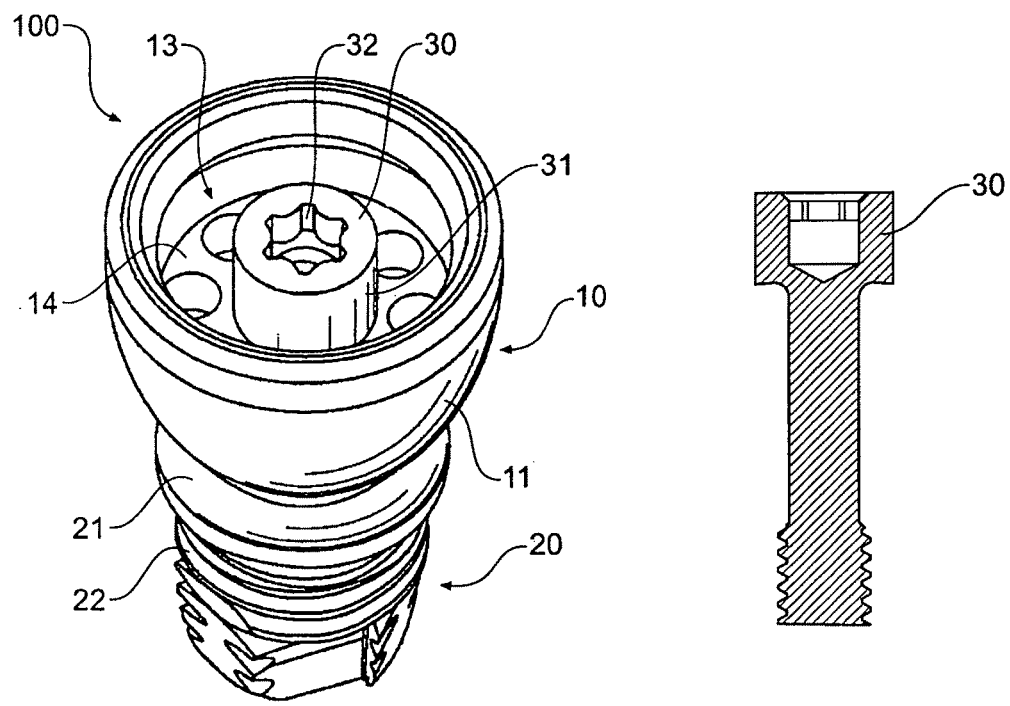
FIG. 3—shows a perspective view of the medical implant system of FIG. 1.

FIG. 3 shows a perspective view of the medical implant system 100. In this view, the abutment interior 13 is visible, showing the abutment interior base 14. Also visible in this view is abutment screw 30 with head 31 and hexagonal well 32. The fixture 20 with base collar 21 and outer screw thread 22 is also visible.

Figure 4:
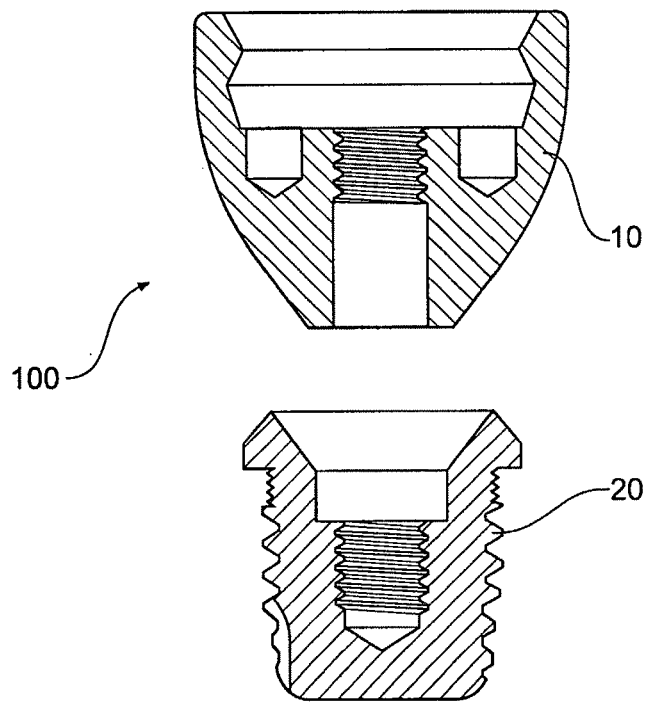
FIG. 4—shows a cross section exploded view of the components of the medical implant system of FIG. 1.

FIG. 4 shows a cross section view of three constituent parts of the medical implant system 100, with those parts separated from one another for clarity. There shown are abutment screw 30, abutment 10 and fixture 20.

FIG. 5A shows an exemplary embodiment of abutment screw 30. In particular, abutment screw head includes a base 35 which includes a deformable element in the form of a flange 36, which is angled downwards and outwards away from the head at a flange angle of about 10 degrees (in one example), as is more clearly seen in FIG. 5C. FIGS. 5B and 5C show a cross section view of the abutment screw 30 of FIG. 5A. In these views, the deformable element in the form of the flange 36 is more clearly visible.

In one embodiment, the outer portion of the flange 36, corresponding to at least part of the deformable element of the abutment screw 30, has a flat portion 37 (see FIG. 5C) which, in use, rests on a corresponding contact surface, in this case, the abutment interior base 14 as shown in FIG. 6. The deformable element is able to deform to form a seal. In one example, when the abutment screw 30 is screwed down into the inner screw thread 23 of fixture 20, flat portion 37 comes into contact with the corresponding contact surface or abutment interior base 14. When the abutment screw 30 is screwed further downwards, the deformable element corresponding to flange 36 with flat portion 37 is pressed downwards (which may cause the edge to move outwards) against the corresponding contact surface or abutment interior base 14 and thereby deform to provide a seal between the abutment screw 30 and the corresponding contact surface, in this case abutment interior base 14. In other words, the deformable element deforms a sufficient amount to provide a seal between the abutment screw 30 and the abutment 10, upon tightening of the abutment screw 30.

In other examples, the deformable element may deform upon application of downward pressure on the implant system or on a part thereof, such as on the screw head 31.

In the various examples detailed herein and/or variations thereof, the type of deformation may be plastic, elastic or a combination of both.

Figure 28:
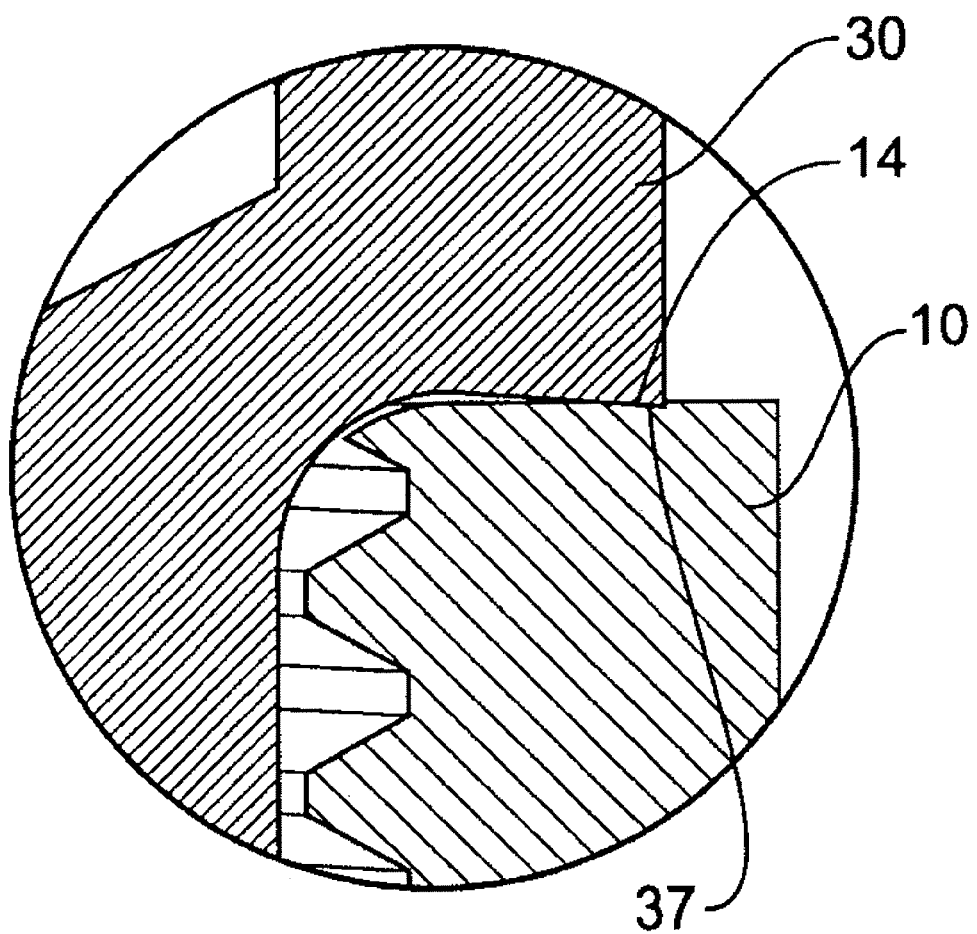
FIG. 28—shows a close-up cross section view of a seal provided between the abutment screw of FIG. 5*a* and the abutment in an alternate embodiment.

FIG. 7 shows a close up view of this engagement between the abutment screw 30 and the abutment 10, and in particular, shows how the deformation of the deformable element as flange 36 and the flat portion 37 is deformed and pressed into the surface of the abutment interior base 14, to provide a seal. In some cases, the corresponding contact surface, in this case the abutment interior base 14, may itself also deform slightly to further increase the seal formed therebetween. In the same vein, FIG. 28 shows a close up view of engagement between the abutment screw 30 and the abutment 10 in an alternate embodiment, which depicts the flange 36 being pressed into the surface of the abutment interior base 14, to provide a seal. As will be understood from FIG. 28, in this alternate embodiment, the corresponding contact surface, in this case the abutment interior base 14, may itself deform slightly to further increase the seal formed therebetween. The degree of resulting deformation of the abutment screw and/or the abutment may vary between embodiments. In some embodiments, all or substantially all of the overall deformation may occur in the abutment screw 30, while in some embodiments, all or substantially all of the deformation may occur in the abutment 10, while in some embodiments, the amount of deformation may be more evenly distributed between these two components.

As the contact surface increases by the deformation of the flange 36 and/or the abutment interior base 14, surface imperfections between the contacting surfaces might be compensated for, which reduces any gaps or holes for microbes (including fungi and bacteria) to pass through from the outside into the inside of the abutment.

This thereby provides a seal at the abutment and abutment screw interface, to reduce the risk of bacterial infection via the micro leakage pathway.

While the screw head 31 of abutment screw 30 may in some embodiments, have a well 32 as shown in FIGS. 5A, 5B, 5C and 6, which may assist in providing the deformable element as flange 36, in other embodiments, head 31 need not have a well. Further, the deformable element may be provided by any suitable structure, and may include the provision of an annular relief 38 above flange 36 to enhance the deformation, as shown in FIG. 8.

The screw head 31 of abutment screw 30 may in some embodiments, have a screw thread which may assist in providing the deformable element as flange 36 (not shown).

Figure 29:
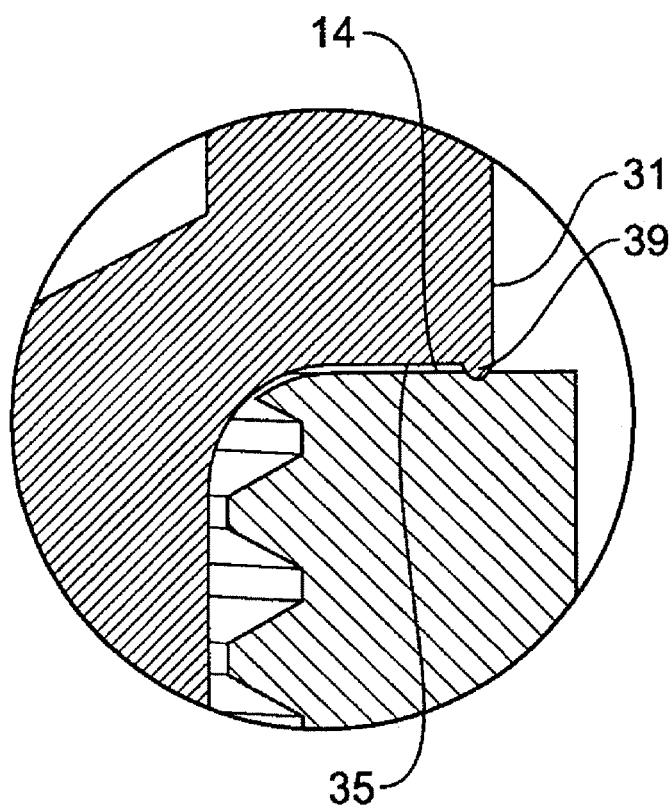
FIG. 29—shows a close-up cross section view of a seal provided between the abutment screw of FIG. 9*a* and the abutment in an alternate embodiment.

In another embodiment, as shown in a cross section view in FIG. 9A, the deformable element may be provided on the base of the head 31 by way of an annular ring 39 extending about the outer edge of the abutment screw head base 35. FIG. 9B shows a perspective view of this arrangement. As in the previous example, when abutment screw 30 is tightened into position, the deformable element in the form of annular ring 39, is deformed so as to form a seal between the abutment screw 30 and the abutment 10. FIG. 10 shows a close up view of this seal formed by the deformation of the deformable element. Again, in some cases, the abutment interior base 14 may also be slightly deformed. In the same vein, FIG. 29 shows an alternate embodiment where the deformable element is located again on the interior 14 abutment 10, and element 39 presses into the abutment 10, thereby forming a seal. In another embodiment, the deformable element in the form of the annular ring may be provided on the abutment itself. As may be seen from FIG. 10 the deformable element may be a protrusion having a triangular cross-section or semi-circular cross section extending from a generally planar surface of a component of the medical implant.

Figure 11:
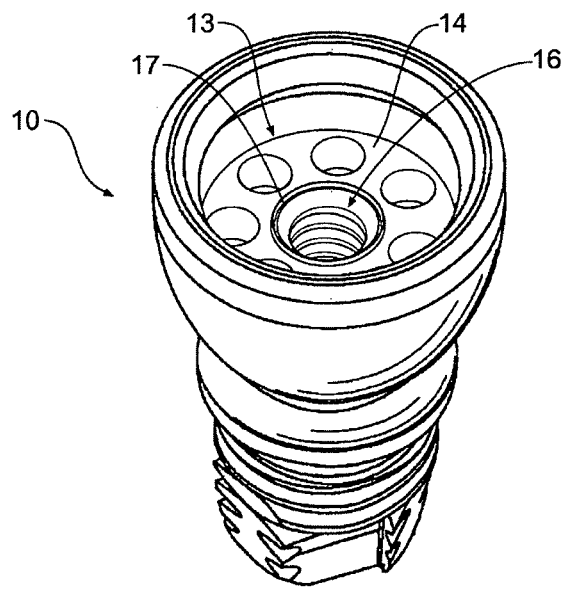
FIG. 11—shows a perspective view of one embodiment of an abutment.
Figure 12:
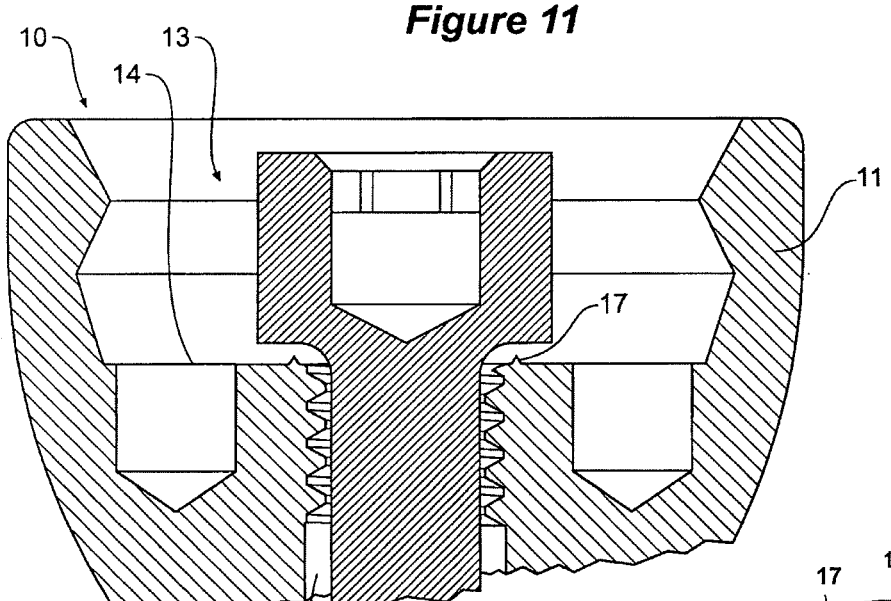
FIG. 12—shows a cross section of the abutment of FIG. 11.

FIG. 11 shows a perspective view of abutment 10 showing abutment interior 13 providing an abutment receiving well for receiving the abutment 10, and abutment interior base 14. Without abutment screw 30, the through bore 16, into which abutment screw 30 is inserted in use, is visible. In this embodiment, the deformable element is provided by an annular ring 17 surrounding the through bore 16. FIG. 12 shows a cross section view of abutment 10 with annular ring 17 surrounding through bore 16. Again, as abutment screw 30 is inserted into through bore 16 and tightened, the base 35 (in this case providing the corresponding contact surface) of head 31 will be compressed over deformable element, in this case, annular ring 17, so as to deform it to provide a seal between abutment screw 30 and abutment 10. This again provides a barrier to bacteria entry into the micro leakage path and reduces risk of infection. In this case, the base 35 of head 31 may be planar rather than angled as in a previous example.

Figure 13:
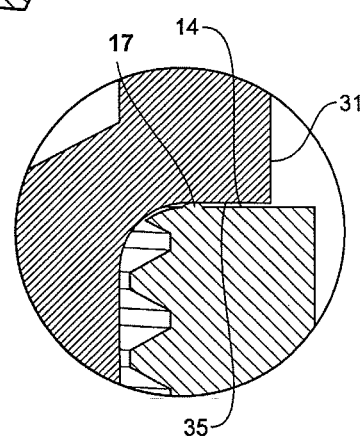
FIG. 13—shows a close-up view of a seal provided between the abutment screw and the abutment of FIG. 11.
Figure 30A:
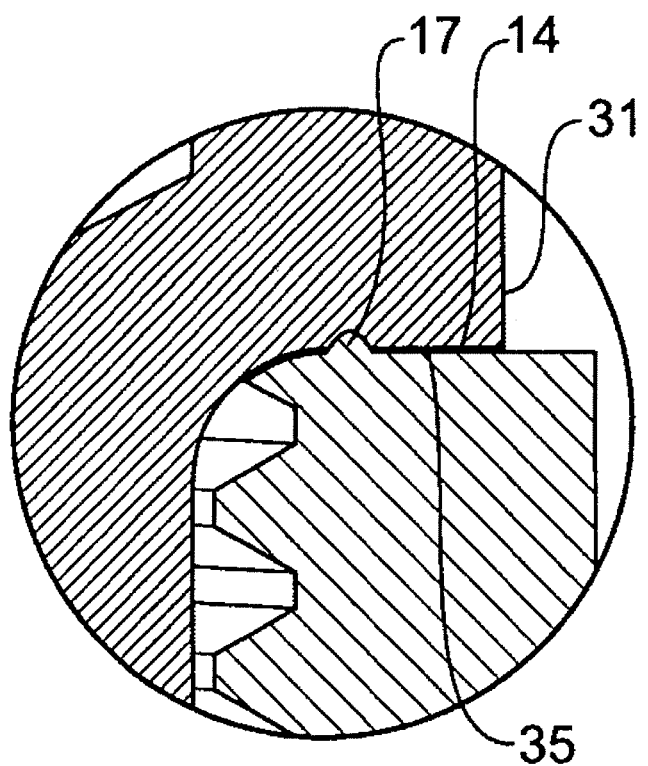
FIG. 30*a*—shows a close-up view of a seal provided between the abutment screw and the abutment of FIG. 11 in an alternate embodiment.

FIG. 13 shows a close up view of the seal so formed, showing the deformation of deformable element, in this case, annular ring 17. FIG. 30*a* shows an alternate embodiment where the deformable element is located on the abutment screw 30 and element 17 presses into the screw 30, thereby forming a seal.

In one example, the height of annular ring 17 is about 0.05 mm and the width of annular ring 17 is about 0.05 mm (prior to deformation). Of course, any other suitable dimensions may be used, including but not limited to about 0.01 mm to about 0.1 mm, about 0.04 mm, about 0.06 mm, about 0.03 mm and about 0.07 mm or any combination thereof.

The above embodiments have provided examples of forming the seal between the abutment screw 30 and the abutment 10. In other embodiments and aspects, the seal may alternatively, or also, be formed between the fixture 20 and the abutment 10, as will now be detailed.

Figure 14:
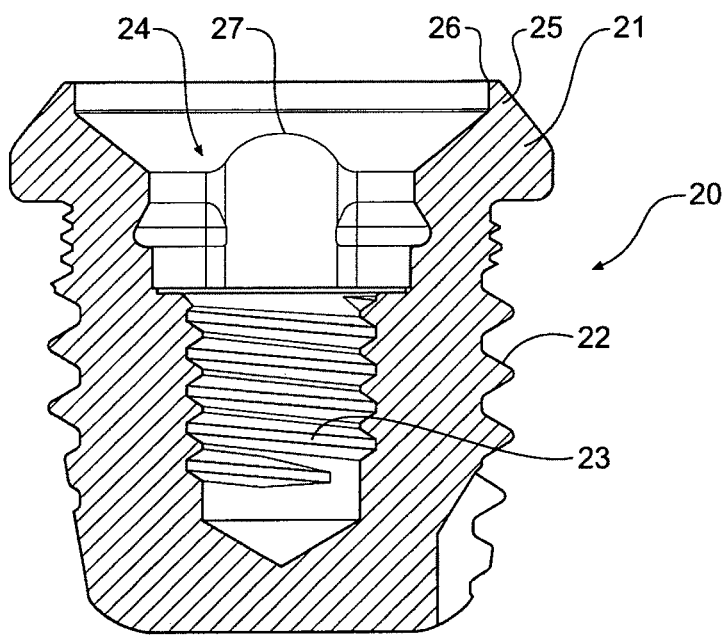
FIG. 14—shows a cross section of one embodiment of a fixture.
Figure 15:
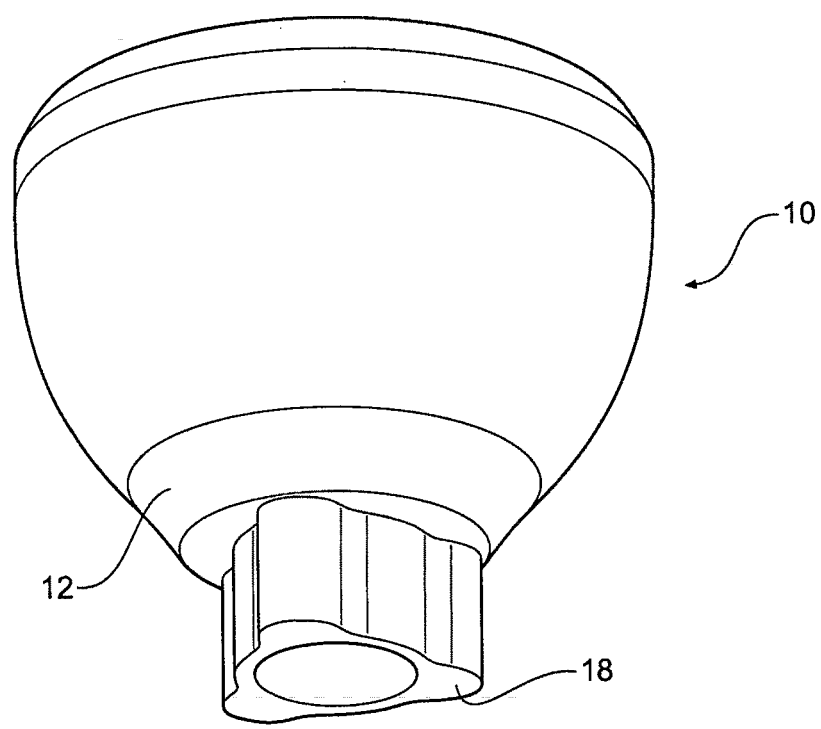
FIG. 15—shows a perspective v one embodiment abutment for use with the fixture of FIG. 14.
Figure 16:
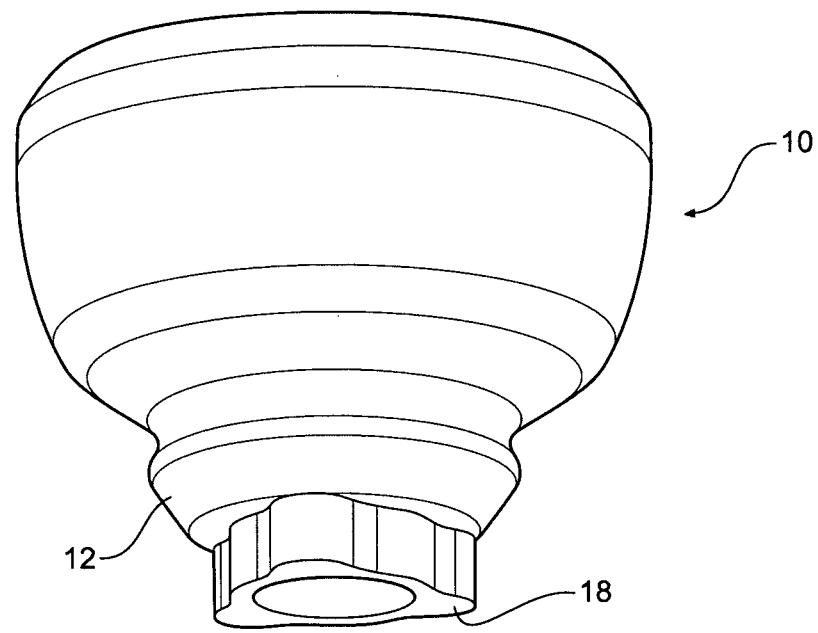
FIG. 16—shows a perspective view of another embodiment of an abutment for use with the fixture of FIG. 14.
Figure 17:
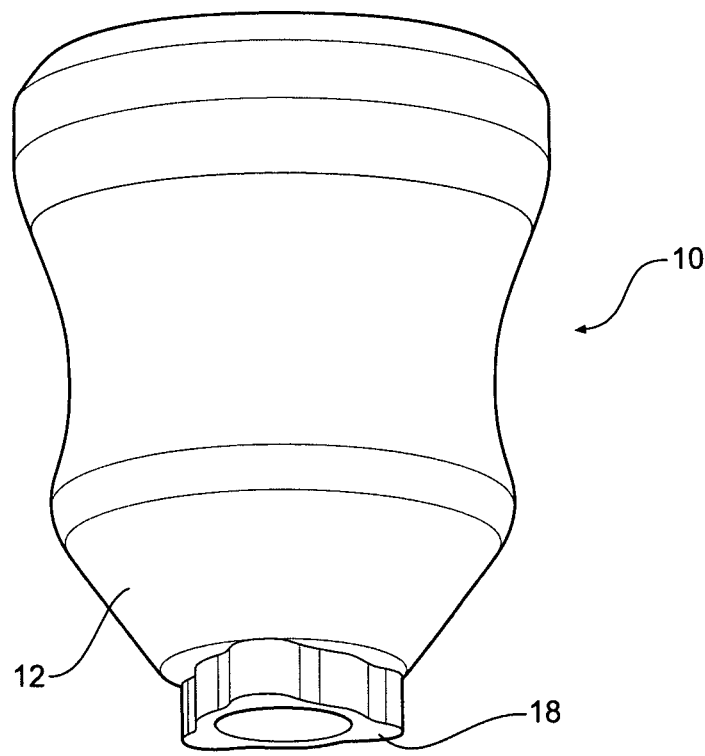
FIG. 17—shows a perspective view et another embodiment of an abutment for use with the fixture of FIG. 14.

In one embodiment of this aspect, as shown by way of example in FIG. 14, fixture 20 is provided with an annular corner 26 on lip 25 of the abutment receiving well, which defines the fixture interior 24. The abutment base 12 of abutment 10 is received in fixture interior 24 to be retained by tightening the abutment screw 30 as previously described. FIGS. 15, 16 and 17 show various examples of abutment 10 configurations that may be used in this aspect.

In some exemplary embodiments of this aspect of the present invention, the fixture interior 24 of the fixture 20 has a bottom geometrical configuration, for instance a lobe shaped geometrical configuration 27, and the protruding bottom part of the abutment 10 has a corresponding geometrical configuration 18 as illustrated in FIGS. 15, 16 and 17, to prevent otherwise resist against rotation between these two parts when coupled together.

Figure 18:
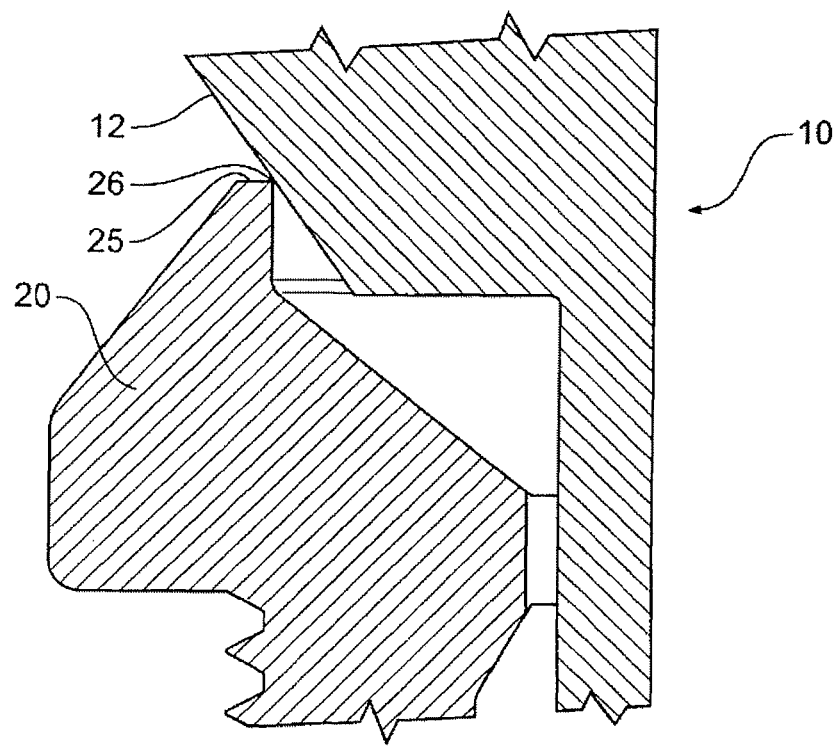
FIG. 18—shows the abutment of any one of FIGS. 15 to 17 in place in the e fixture of FIG. 14.

The abutment 10 may have a substantially curved, conical outer surface with the upper edge having the wider diameter and the bottom, fixture-connecting part having a smaller diameter, as illustrated. A feature in these particular embodiments for the three different examples of abutments 10 illustrated in FIGS. 15, 16 and 17 may be that the bottom tapered outer surface 12 which cooperates with the annular corner 26 of the fixture 20 when the two parts are coupled together as shown in FIG. 18. This provides a concave outer contour of the connection between the abutment and the fixture.

Figure 19:
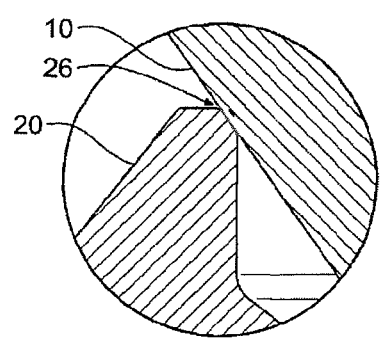
FIG. 19—shows a close-up view of the seal provided by the arrangement of FIG. 18.

In this example, the deformable element is provided by the annular corner 26. When the abutment 10 is placed in the fixture 20 and the abutment screw 30 is lightened as previously described, the abutment base 12, (in this case acting as the corresponding contact surface) is pressed down onto annular corner 26, which deforms to provide a seal between abutment 10 and fixture 20. FIG. 19 shows a close up view of the seal formed therebetween.

The deformable element may also deform upon application of other force, such as by downward pressure on abutment 10, rather than, or in conjunction with, tightening of the abutment screw 30.

In some embodiments, the outer surface of the abutment 10 and/or the fixture 20 might be modified in order to improve the skin tissue integration. Different types of structured or coated surfaces might be used, for instance hydroxyapatite (HA) coated surfaces. In this case it should be understood that the coating might be applied on the fixture and the abutment separately, or applied on a pre mounted implant device.

Figure 30B:
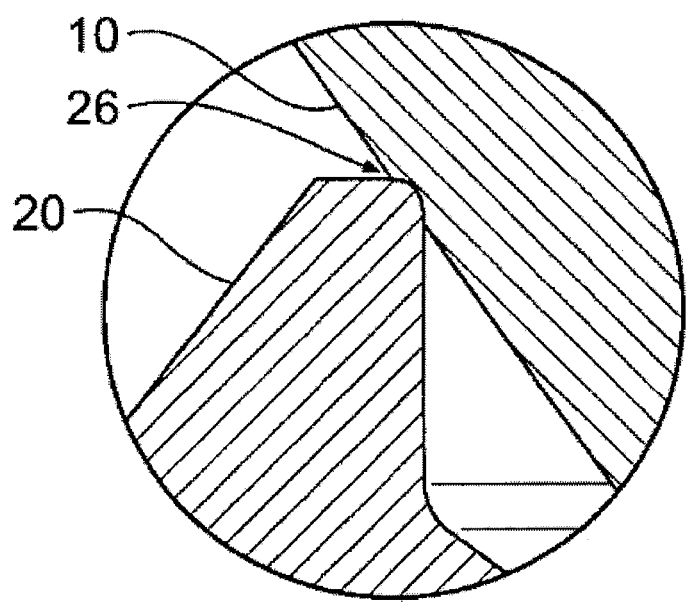
FIG. 30*b*—shows a close-up view of the seal provided by the arrangement of FIG. 18 in an alternate embodiment.

In a further embodiment of this aspect, the deformable element may be provided on the abutment 10 as shown in FIG. 30*b*, which corresponds to the view of FIG. 19, and, in some embodiments, the deformable element may be in the form of an annular ring, as depicted in FIGS. 20 and 21. In the embodiment of FIG. 20, the deformable element is provided by abutment annular corner 19 on the abutment base 12. In this embodiment, the lip 25 of fixture 20 may be a more conventional rounded shape, which provides the corresponding contact surface for the deformable element, in this case, abutment annular corner 19. As in the previous example, abutment 10 is placed in the fixture 20 and when abutment screw 30 is tightened, abutment 10 is pressed down onto fixture 20. In this arrangement, deformable element (abutment annular corner 19) will be deformed against the lip 25 to form a seal between the abutment 10 and the fixture 20.

FIG. 22 is a close up view of the seal formed between the abutment 10 and the fixture 20 of FIG. 21.

Figure 23:
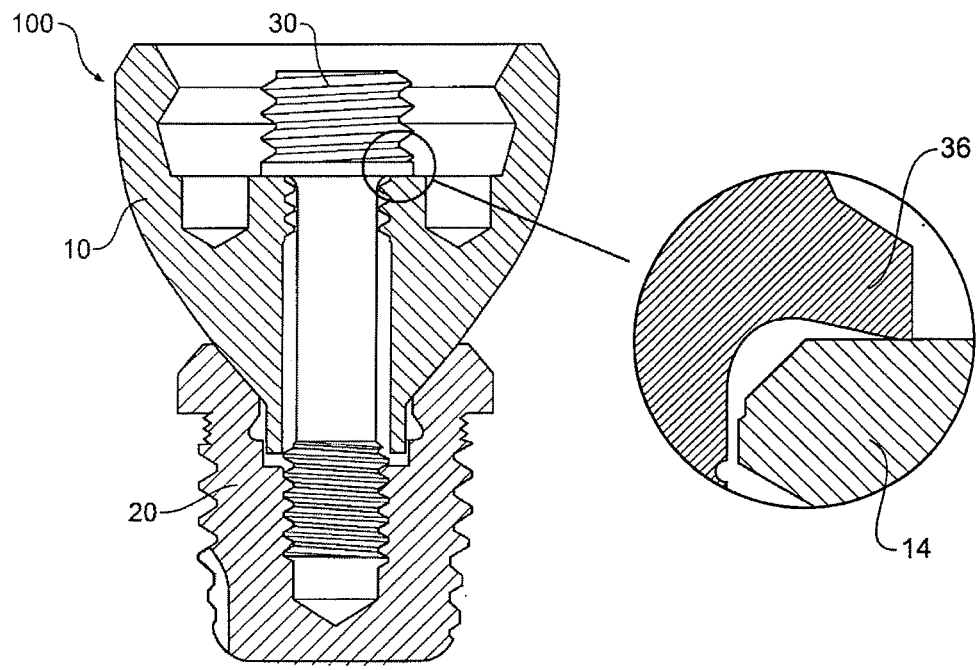
FIG. 23—shows an embodiment of a medical implant system with a seal provided between the abutment and the abutment screw.
Figure 31:
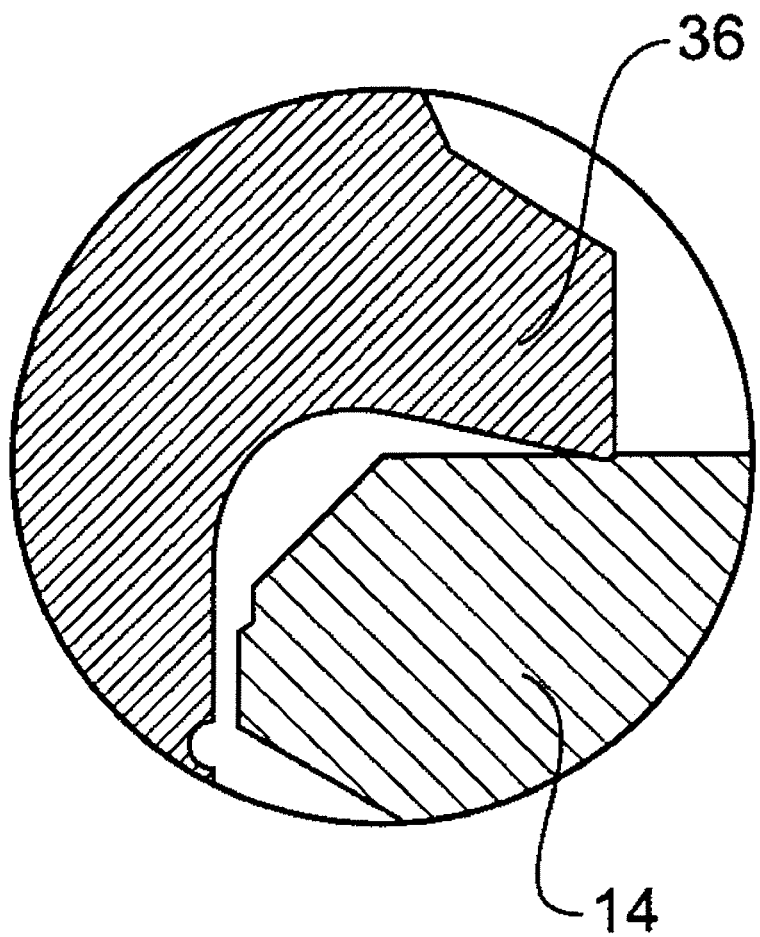
FIG. 31—shows an alternate embodiment of a medical implant system with a seal provided between the abutment and the abutment screw.

FIG. 23 shows an example of another embodiment of a medical implant system 100, comprising abutment 10, fixture 20 and abutment screw 30. In this example, the system is designed so as to provide a seal between the abutment 10 and the abutment screw 30. In this case, this seal is provided by an arrangement similar and/or the same as that described earlier with reference to FIGS. 5A, 5B, 5C, 6 and 7. With respect to the embodiment of FIG. 23, the deformable element is provided on the abutment screw 30 in the form of an angled flange that upon tightening of abutment screw 30 (or application of other force), deforms against the corresponding contact surface (in this case abutment interior base 14) to form the seal. FIG. 31 depicts an alternate embodiment where engagement between the abutment screw 30 and the abutment 10 is depicted, and the abutment interior base 14 of abutment 10 deforms. Specifically, flange 36 is pressed into the surface of the abutment interior base 14, to provide a seal. As will be understood from FIG. 31, in this alternate embodiment, the corresponding contact surface, in this case the abutment interior base 14, may itself deform slightly to further increase the seal formed therebetween. The degree of resulting deformation of the abutment screw and/or the abutment may vary between embodiments. In some embodiments, all or substantially all of the overall deformation may occur in the abutment screw 30, while in some embodiments, all or substantially all of the deformation may occur in the abutment 10, while in some embodiments, the amount of deformation may be more evenly distributed between these two components.

Figure 24:
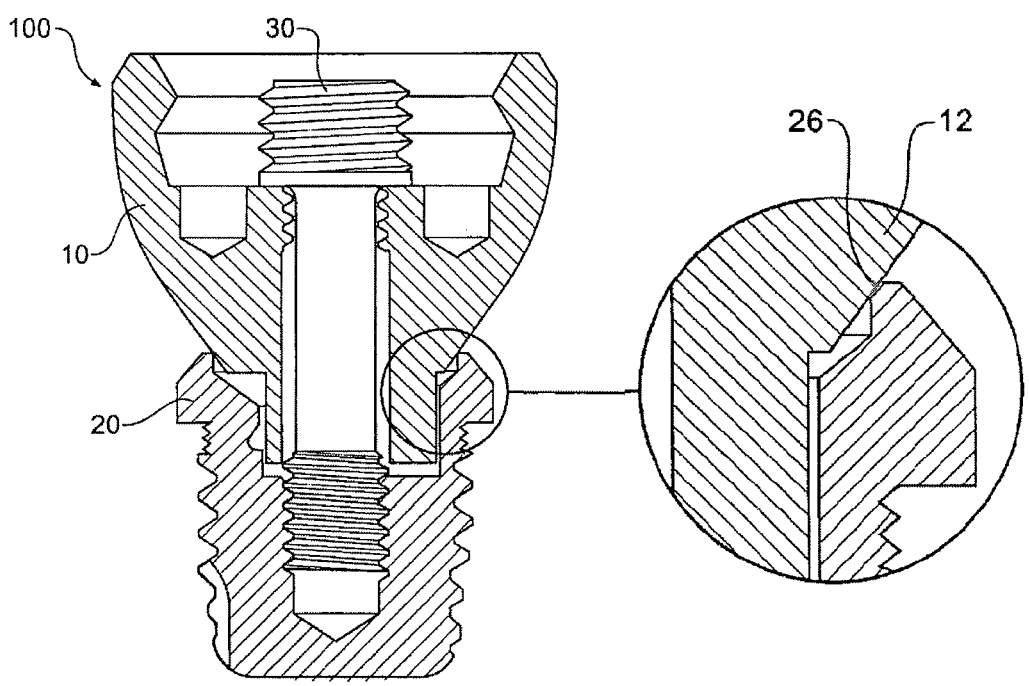
FIG. 24—shows another embodiment of a medical implant system with a seal provided between the abutment and the fixture.
Figure 32:
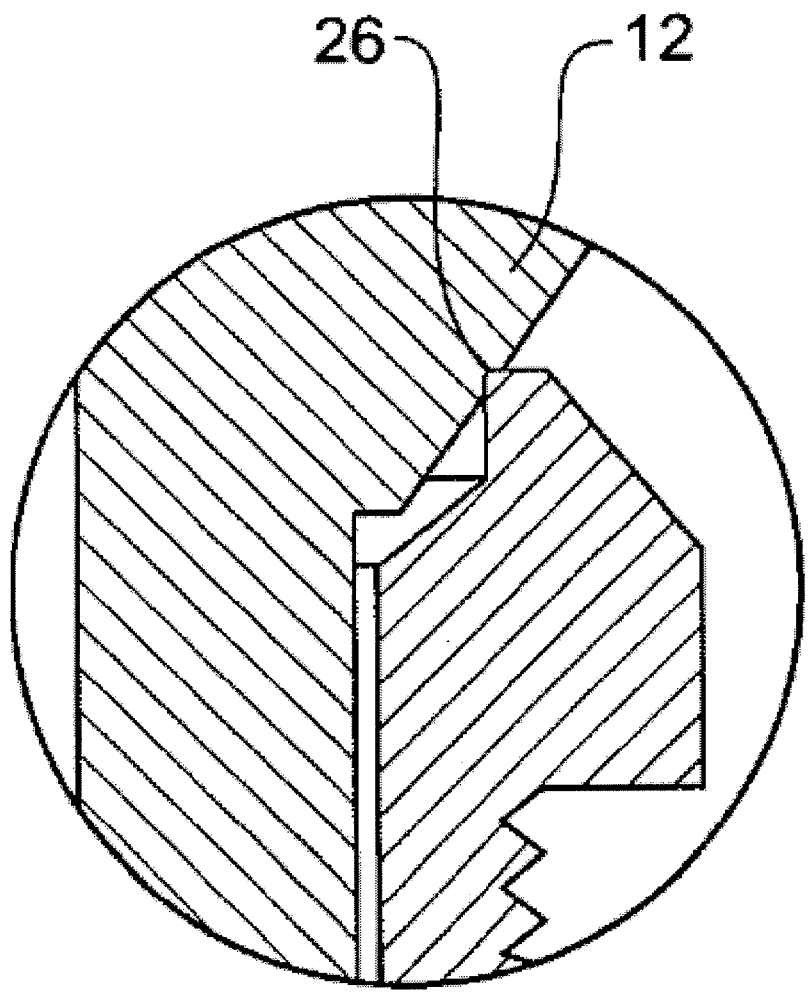
FIG. 32—shows another embodiment of a medical implant system with a seal provided between the abutment and the fixture.

FIG. 24 shows another embodiment of a medical implant system 100 comprising abutment 10, fixture 20 and abutment screw 30. In this example, the system is designed to provide a seal between abutment 10 and fixture 20. In this case, the seal is provided by the same arrangement as described earlier with reference to FIGS. 14 to 19. That is, that the deformable element is provided on the fixture 20 in the form of an annular corner 26 provided on the lip 25 of fixture 20, that upon tightening of abutment screw 309 or application of other force), deforms against the corresponding contact surface (in this case abutment base 12) to form the seal. FIG. 32 depicts an alternate embodiment where engagement between the bone fixture 20 and the abutment 10 is depicted. The depicted deformation of the abutment 10 is a result of the annular corner 26 of lip 25 of the fixture 70 being pressed into the surface of the abutment 10, to provide a seal. As will be understood from FIG. 32, in this alternate embodiment, the corresponding contact surface, in this case the annular corner 26, may itself deform slightly to further increase the seal formed therebetween. The degree of resulting deformation of the fixture 20 and/or the abutment 10 may vary between embodiments. In some embodiments, all or substantially all of the overall deformation may occur in the abutment 10, while in some embodiments, all or substantially all of the deformation may occur in the bone fixture 20, while in some embodiments, the amount of deformation may be more evenly distributed between these two components.

Figure 25:
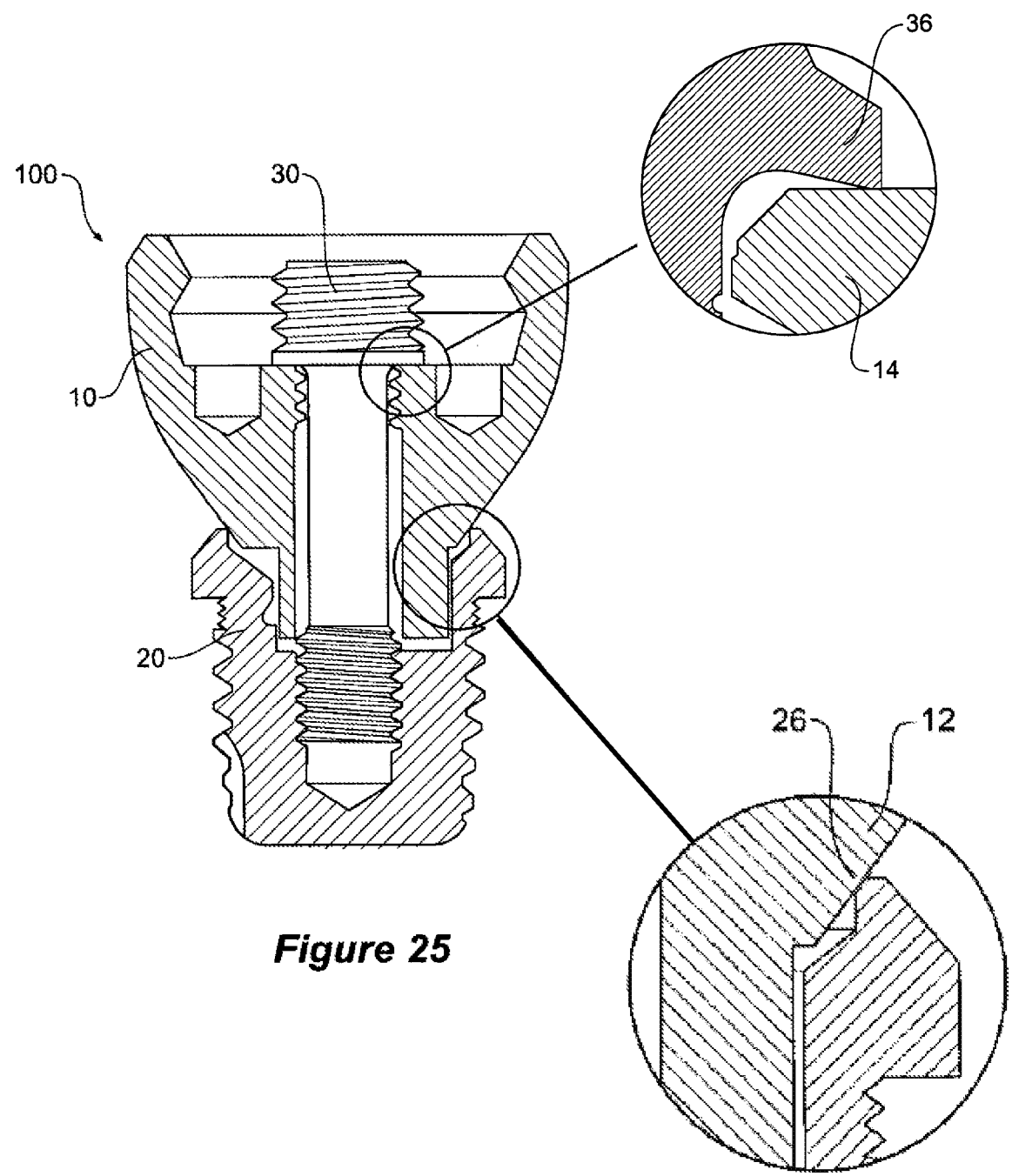
FIG. 25—shows another embodiment of a medical implant system with a seal provided between the abutment and the abutment screw as well as between the abutment and the fixture.

FIG. 25 shows yet another embodiment of a medical implant system 100 comprising abutment 10, fixture 20 and abutment screw 30. In this example, the system is designed to provide a seal between the abutment 10 and the abutment screw 30 as well as between the abutment 10 and fixture 20. In this case, the first seal is provided by the same arrangement as described above with reference to FIG. 23. That is, that the deformable clement is provided on the abutment screw 30 in the form of an angled flange that upon tightening of abutment screw 30 (or application of other force), deforms against the corresponding contact surface (in this case abutment interior base 14) to form the seal. The second seal is provided by the arrangement described above with reference to FIG. 24. That is, that the deformable element is provided on the fixture 20 in the form of an annular corner 26 provided on the lip 25 of fixture 20, that upon tightening of abutment screw 30 9 or application of other force), deforms against the corresponding contact surface (in this case abutment base 12) to form the seal. Accordingly, the arrangement of FIG. 25 is a combination of both the arrangements of FIGS. 23 and 24.

Figure 33:
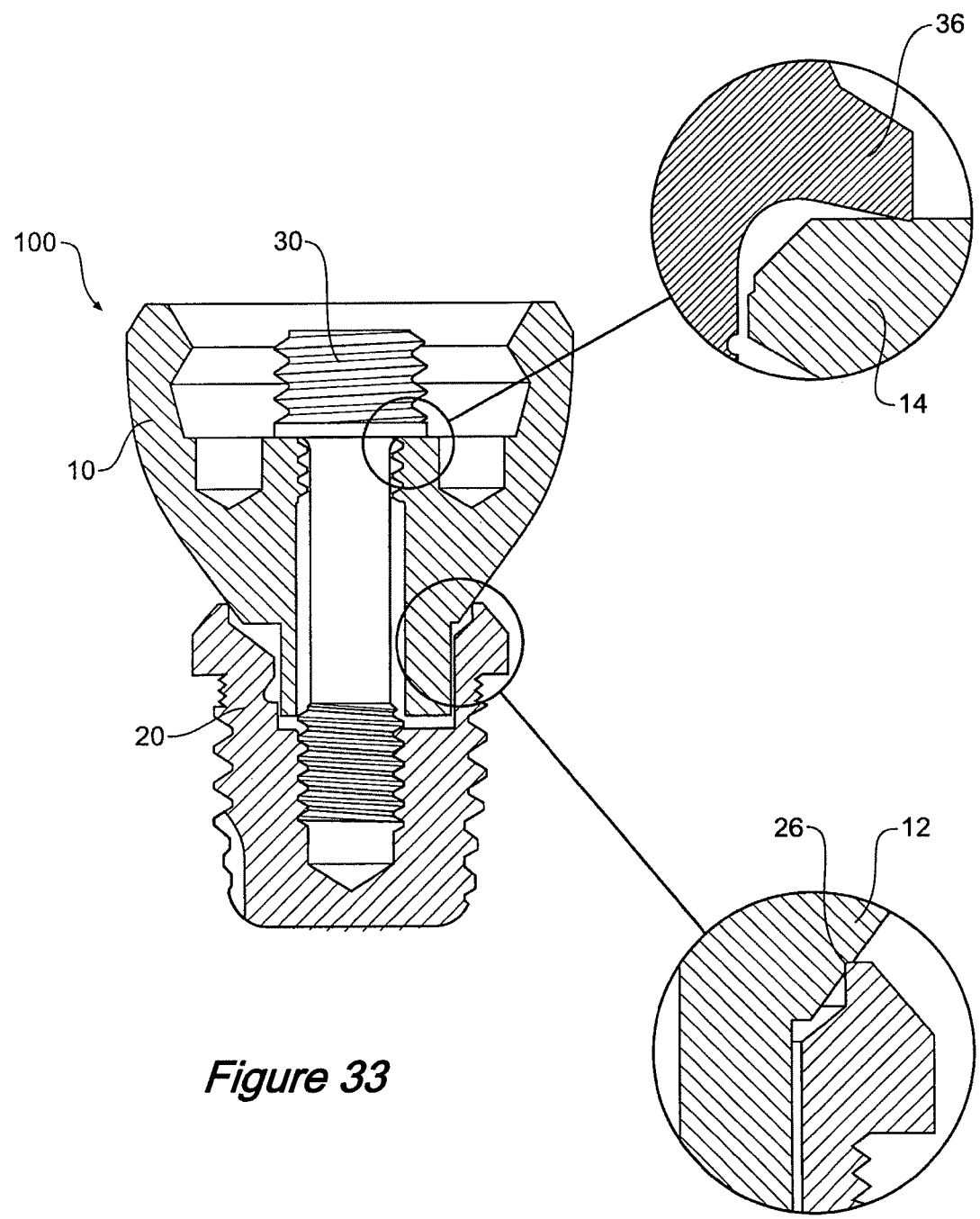
FIG. 33—shows another embodiment of a medical implant system with a seal provided between the abutment and the abutment screw as well as between the abutment and the fixture.

In yet further embodiments, any combination of any two or more of the seals previously described may be used, including two different seals provided between the abutment 10 and the abutment screw 30 as shown in FIGS. 5 to 10 as well as FIGS. 11 to 13. By way of example, FIG. 33 depicts yet another embodiment of a medical implant system 100 comprising abutment 10, fixture 20 and abutment screw 30. In this example, the system is designed to provide a seal between the abutment 10 and the abutment screw 30 as well as between the abutment 10 and fixture 20. In this case, the first seal is provided by the alternate arrangement as described above with reference to FIG. 23 and FIG. 31. That is, that the deformable element is provided on the abutment 10 (in this case this case, abutment interior base 14) such that that upon tightening of abutment screw 30 (or application of other force), the abutment 10 deforms against the corresponding contact surface of the abutment screw 30 to form the seal. The second seal is provided by the arrangement described above with reference to the alternate arrangement described above with reference to FIG. 24 and FIG. 32. That is, that the deformable element is again provided on the abutment 10 (in this case, abutment base 12) such that upon tightening of abutment screw 30 (or application of other force), the abutment 10 deforms against the corresponding contact surface (annular corner 26 provided on the lip 25 of fixture 20) to form the seal. Accordingly, the arrangement of FIG. 25 is a combination of both the alternate arrangements of FIGS. 23 and 24 described above.

It will be appreciated that the various deformable elements described may be provided by any suitable means, including by turning, during or after the usual component production process.

The provision of the deformable clement(s) in the various components of the medical implant system 100 provide for a unique method of implanting the medical implant system.

The steps of one possible method of implanting the medical implant system 100 are shown in FIG. 26a. At step 200, the abutment 10 is located in the abutment receiving well of fixture interior 24 of the already implanted fixture. At step 201, the abutment screw 30 is inserted in the through bore 16 of the abutment 10 and into the fixture 20. In step 202, force is applied to the implant system until the deformable element(s) deforms to provide the seal(s) between the various components of the medical implant system, thereby reducing the risk of infection in the user or patient. In one example, the force may be applied by way of pressure on the abutment.

In another example, as shown in FIG. 26b, the same steps 200 and 201 may be used, however, in step 202', the force may be applied by way of tightening the abutment screw 30. In one example, the abutment screw is tightened using a torque of greater than about 15 Ncm, and including about 15 Ncm to about 20 Ncm, and about 20 Ncm to about 30 Ncm. In one particular example, the torque used is about 25 Ncm.

In some embodiments, the, or part of, the surfaces of one or more of the components, such as the abutment screw 30 may be coated with a friction-reducing material such as diamond like carbon (DLC). In these embodiments, the required torque or other force will be reduced.

Figure 27B:
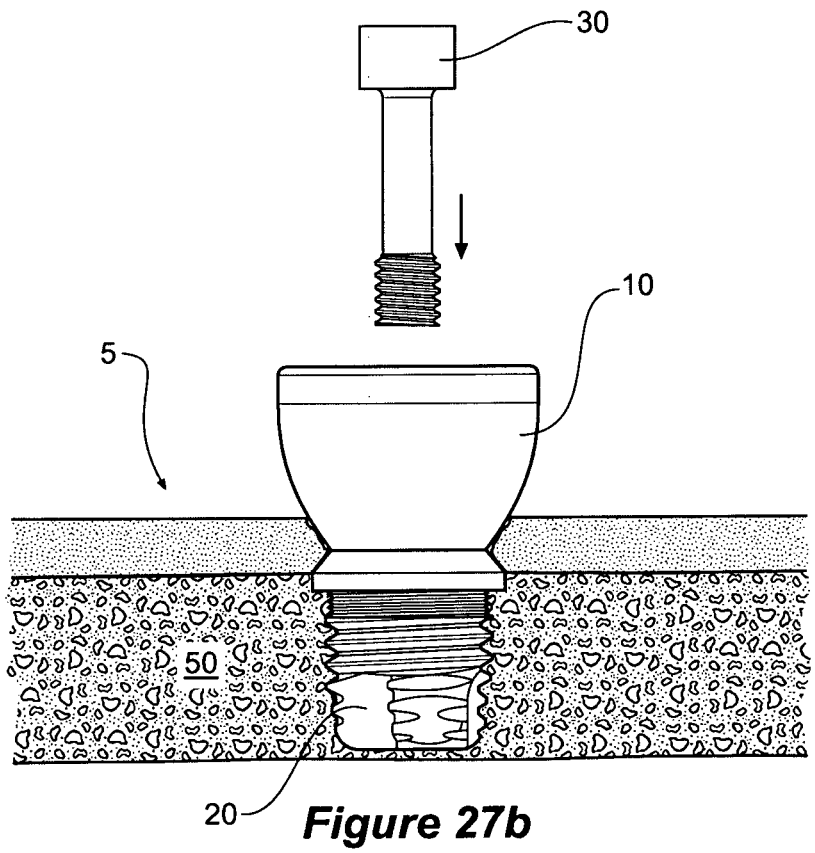
FIG. 27*b*—shows a cross section of the arrangement of the second step of the method of FIG. 26*b*.
Figure 27C:
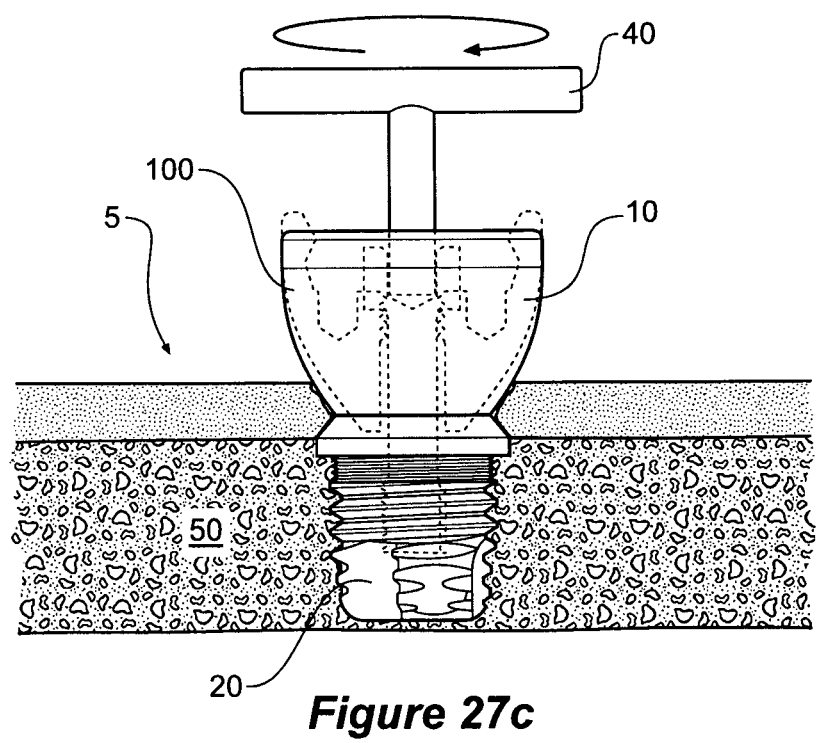
FIG. 27*c*—shows a cross section of the arrangement of the third step of the method of FIG. 26B.
Figure 27D:
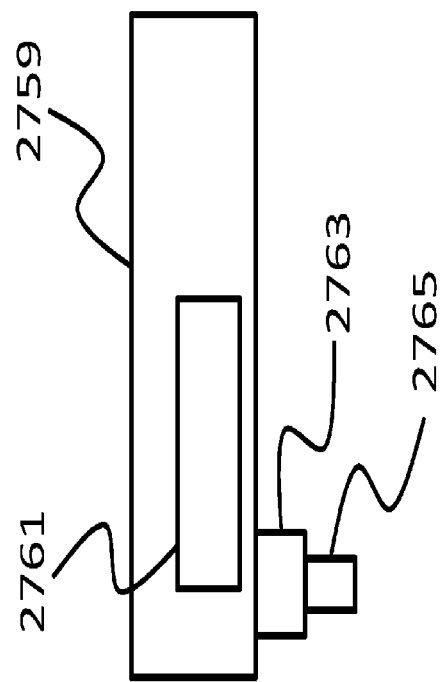
FIG. 27*d*—shows in black-box format a functional conceptual external removable unit of a percutaneous bone conduction device including a vibrator, along with an implant.

FIGS. 27a, 27b and 27c illustrate these steps 200, 201 and 202'. In FIG. 27a, the abutment 10 is located inside fixture 20. In this example, fixture 20 has already been implanted and anchored in the bone 50 of the patient's skull, in a previous procedure and allowed to heal. This example method therefore begins with the location of the abutment 10 in fixture 20. This is done through an opening created in the tissue 5 of the patient.

In FIG. 27b, the abutment screw 30 is inserted into the abutment 10 and the fixture 20 and in FIG. 27c, the abutment screw 30 is tightened using an insertion tool 40. This tightening causes any deformable elements in the system to deform and form seals to reduce the risk of bacteria entering into the micro leakage path and thus reducing risk of infection.

The seals may be provided as previously described, between the abutment screw 30 and the abutment 10, the abutment 10 and the fixture 20, or both, with the locations of these discernible from the dotted lines superimposed on FIG. 27c.

Embodiments utilizing multiple deformable elements may use different types of deformable elements/deformable elements of different geometries as detailed herein and/or variations thereof.

In view of the above, it can be seen that in at least one aspect of the invention, there is a medical implant system for attaching a hearing device to a user is provided. In one form, the medical implant system comprises a fixture, an abutment and an abutment screw for connecting the abutment to the fixture. In this aspect, there is provided on one or more of these components, a deformable element that deforms to form a seal between the one or more components of the medical implant system.

In view of the above, it can be seen that in at least one other aspect of the invention, there is an abutment for use in a medical implant system comprising a fixture, the abutment and an abutment screw. In one form, the abutment comprises a through bore for receiving the abutment screw and a deformable element that is deformed against the abutment screw when the abutment screw is inserted in the through bore and tightened.

In view of the above, it can be seen that in at least one other aspect of the invention, there is an abutment screw that comprises a head, an elongate main body and a deformable element that may be deformed between the abutment screw and an abutment to provide a seal upon inserting the abutment screw through the through bore of the abutment and tightening the abutment screw.

In view of the above, it can be seen that in at least one other aspect of the invention, there is a fixture for use in a medical implant system. The fixture comprises a main body, an abutment receiving well and a screw thread for anchoring the fixture into bone. In one form, a deformable element is provided as an annular corner of the abutment receiving well.

In view of the above, it can be seen that in at least one other aspect of the invention, there is a method of implanting a medical implant system into a user. The medical implant system comprises a fixture, an abutment and an abutment screw. The method involves locating the abutment in an abutment receiving well of the fixture, inserting the abutment screw in a through bore of the abutment and into the fixture, and applying a force to the implant. In one form, this force is provided by tightening the abutment screw until a deformable element deforms to provide a seal between one or more of the components of the implant system.

In some embodiments, the seals formed by the embodiments detailed herein and/or variations thereof may form a hermetic seal. In some embodiments, the seal is an air tight seal.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

It will be understood that the invention disclosed and defined in this specification extends to all alternative combinations of two or more of the individual features mentioned or evident from the text or drawings. All of these different combinations constitute various alternative aspects of the invention.

While various embodiments of the present technology have been described above, it should be understood that they have been presented by way of example only, and not limitation, it will be apparent to persons skilled in the relevant art that various changes in form and detail can be made therein without departing from the spirit and scope of the technology. For instance, features described as part of one implementation can be used on another implementation to yield a still further implementation. Thus, the breadth and scope of the present technology should not be limited by any of the above-described exemplary embodiments, but should be defined only in accordance with the following claims and their equivalents. All patents and publications discussed herein are hereby incorporated in their entirety by reference thereto.

What is claimed is:

1. A bone conduction hearing prosthesis implant, comprising:
    a bone fixture configured to anchor to bone of a recipient;
    a structural component configured to be connected to the bone fixture and connect a functional component of the implant to the bone fixture; and
    a screw configured to bolt the structural component to the bone fixture, wherein the implant includes an anti-microbial seal between the structural component and the screw, wherein
    the anti-microbial seal is established by features that have, prior to deformation of one or more portions of the screw or the structural component that establish the anti-microbial seal:
        a ridge on one of the screw or the structural component; and
    a flat surface on the other of the screw or the structural component, wherein the ridge interfaces with the flat surface to result in deformation of at least the ridge to establish the anti-microbial seal,
    the ridge is monolithic with the screw or the structural component and the flat surface is monolithic with the other of the screw or the structural component,
    the screw comprises a head atop an elongate main body, the head having a base, wherein the seal is located between the base of the head and an inboard portion of the structural component,
    tightening the screw relative to the bone fixture causes the deformation of the one or more portions of the screw or the structural component to establish the anti-microbial seal,
    the flat surface is normal to a longitudinal axis of the implant, and
    the structural component is a skin-penetrating abutment.

2. The bone conduction hearing prosthesis implant of claim 1, further comprising:
    an annular relief configured to enhance the deformation of the ridge.

3. The hone conduction hearing prosthesis implant of claim 1, wherein:
    the screw includes a friction-reducing coating.

4. The hone conduction hearing prosthesis implant of claim 1, wherein:
    the screw includes an annular angled ring extending outward and downward from the head; and
    the annular angled ring establishes the ridge.

5. The bone conduction hearing prosthesis implant of claim 1, wherein:
    the head has male threads.

6. The bone conduction hearing prosthesis implant of claim 1, wherein:
    the screw comprises two opposite ends, each end having male threads.

7. The bone conduction hearing prosthesis implant of claim 1, wherein:
    the head has male threads on an outside thereof and a well on an inside thereof, the well being configured to receive a tool to tighten the screw.

8. The bone conduction hearing prosthesis implant of claim 1, wherein:
    the seat is located on the structural component.

9. The bone conduction hearing prosthesis implant of claim 1, wherein:
    the seal is located on the screw.

10. A bone conduction hearing prosthesis implant, comprising:
    a bone fixture configured to anchor to bone of a recipient and configured for installation in bone behind an external ear; and
    a structural component configured to be connected to the bone fixture and connect a functional component of the implant to the bone fixture, wherein at least one of the bone fixture or the structural component includes a deformable portion configured to deform to form an anti-microbial seal between the bone fixture and the structural component, wherein
    the anti-microbial seal is established by features that have, prior to deformation of one or more portions of the structural component that establish the anti-microbial seal;
        a ridge on the structural component; and
        with respect to a cross-section taken parallel to and lying on a longitudinal axis of the bone fixture, a flat surface on the bone fixture, the ridge interfaces with the flat surface to result in deformation of at least the ridge to establish the anti-microbial seal, the ridge having a termination, wherein the deformation of at least the ridge includes deformation of the termination,
the ridge is monolithic with the structural component and the flat surface is monolithic with the bone fixture,
the implant further includes a screw that comprises a head atop an elongate main body, the head having a base,
tightening the screw relative to the bone fixture causes the deformation of the deformable portion to establish the anti-microbial seal,
the screw is a separate component from the structural component, and the structural component is held to the bone fixture b the screw, and
the structural component is a skin-penetrating abutment.

11. The implant of claim 10, wherein:
the ridge is configured to plastically deform to form the anti-microbial seal between the bone fixture and the structural component.

12. The implant of claim 10,
wherein the implant includes an anti-microbial seal between the structural component and the screw.

13. The implant of claim 10, further comprising:
an external removable unit of a percutaneous bone conduction device, wherein the functional component is the external removable unit, the external removable unit including a vibrator, wherein the external removable unit transforms sound into mechanical vibrations, and wherein the external removable unit is coupled to the structural component.

14. The implant of claim 10, wherein:
the bone fixture is configured to be installed in bone behind an external ear of a human; and
the screw has been tightened to cause the deformation of the deformable portion to establish the anti-microbial seal.

15. The implant of claim 13, wherein:
the bone fixture is configured to be installed in bone behind an external ear of a human; and
the screw has been tightened to cause the deformation of the deformable portion to establish the anti-microbial seal.

16. The implant of claim 13, wherein:
the head has male threads.

17. The implant of claim 16, wherein:
the deformation of the ridge is plastic deformation.

18. The implant of claim 14, wherein:
the head has male threads.

19. The implant of claim 18, wherein:
the deformation of the ridge is plastic deformation.

20. The implant of claim 15, wherein:
the head has male threads.

21. The implant of claim 20, wherein:
the deformation of the ridge is plastic deformation.

22. The implant of claim 10, wherein:
the head has male threads.

23. The implant of claim 22, wherein:
the deformation of the ridge is plastic deformation.

* * * * *